(12) United States Patent
Srinath et al.

(10) Patent No.: US 7,645,888 B2
(45) Date of Patent: Jan. 12, 2010

(54) PROCESS FOR THE PRODUCTION OF AMORPHOUS ATORVASTATIN CALCIUM

(75) Inventors: Sumithra Srinath, Bangalore (IN); Joy Matthew, Bangalore (IN); Tom Thomas Puthiaprampil, Bangalore (IN); Sambasivam Ganesh, Bangalore (IN)

(73) Assignee: Biocon Limited, Bangalore, Karnataka (IN)

( * ) Notice: Subject to any disclaimer, the term of this patent is extended or adjusted under 35 U.S.C. 154(b) by 484 days.

(21) Appl. No.: 11/574,354

(22) PCT Filed: Aug. 27, 2004

(86) PCT No.: PCT/IN2004/000265

§ 371 (c)(1),
(2), (4) Date: Feb. 27, 2007

(87) PCT Pub. No.: WO2006/021969

PCT Pub. Date: Mar. 2, 2006

(65) Prior Publication Data

US 2009/0171099 A1    Jul. 2, 2009

(51) Int. Cl.
*C07D 207/34* (2006.01)
*C07D 407/06* (2006.01)
(52) U.S. Cl. .................................. 548/537
(58) Field of Classification Search .................. None
See application file for complete search history.

(56) References Cited

U.S. PATENT DOCUMENTS

| | | | |
|---|---|---|---|
| 5,003,080 A | 3/1991 | Butler et al. |
| 5,097,045 A | 3/1992 | Butler et al. |
| 5,103,024 A | 4/1992 | Millar et al. |
| 5,124,482 A | 6/1992 | Butler et al. |
| 5,149,837 A | 9/1992 | Butler et al. |
| 5,155,251 A | 10/1992 | Butler et al. |
| 5,216,174 A | 6/1993 | Butler et al. |
| 5,245,047 A | 9/1993 | Butler et al. |
| 5,248,793 A | 9/1993 | Millar et al. |
| 5,273,995 A | 12/1993 | Roth |
| 5,280,126 A | 1/1994 | Butler et al. |
| 5,298,627 A | 3/1994 | Butler et al. |
| 5,342,952 A | 8/1994 | Butler et al. |
| 5,385,929 A | 1/1995 | Bjorge et al. |
| 5,397,792 A | 3/1995 | Butler et al. |
| 6,087,511 A | 7/2000 | Lin et al. |

FOREIGN PATENT DOCUMENTS

| | | |
|---|---|---|
| EP | 0409281 A1 | 7/1990 |
| WO | 8907598 A2 | 8/1989 |
| WO | 9703958 A1 | 2/1997 |
| WO | 9703959 A1 | 2/1997 |
| WO | 9703960 A1 | 2/1997 |
| WO | 0071116 A1 | 11/2000 |
| WO | 02059087 A1 | 8/2002 |
| WO | 03099785 A1 | 12/2003 |

*Primary Examiner*—Kamal A Saeed
(74) *Attorney, Agent, or Firm*—Caesar, Rivise, Bernstein, Cohen & Pokotilow, Ltd.

(57) ABSTRACT

A novel process of the preparation of amorphous atorvastatin calcium starting from a compound of Formula (II).

4 Claims, No Drawings

PROCESS FOR THE PRODUCTION OF AMORPHOUS ATORVASTATIN CALCIUM

FIELD OF THE INVENTION

The present invention relates to a novel process for the production of amorphous atorvastatin calcium. Particularly, the present invention relates to a novel process for the production of amorphous atorvastatin calcium from (6-{2-[2-(4-Fluoro-phenyl)-5-isopropyl-3-phenyl-4-phenylcarbamoyl-pyrrolidin-1-yl]-ethyl}-2-phenyl-[1,3,2]dioxaborinan-4-yl)-acetic acid tert-butyl ester.

BACKGROUND OF THE INVENTION

Atorvastatin calcium is known by synonyms like [R—(R*, R*)]-2-(4-fluorophenyl)-☐☐, 6-dihydroxy-5-(1-methylethyl)-3-phenyl-4-[(phenylamino) carbonyy-1h-pyrrole-1-heptanoic acid hemicalcium salt; (☐R,☐R)-2-(4-fluorophenyl)-☐☐-dihydroxy-5-(1-methylethyl)-3-phenyl-4-[(phenylamino)carbonyl]-, 1H-Pyrrole-1-heptanoic acid hemicalcium salt; [R—(R*,R*)]-2-(4-fluorophenyl)-☐☐-dihydroxy-5-(1-methylethyl)-3-phenyl-4-[(phenylamino)carbonyl]-, 1H-Pyrrole-1-heptanoic acid hemicalcium salt or (☐R,☐R)-2-(p-Fluorophenyl)-☐☐-dihydroxy-5-isopropyl-3-phenyl-4-(phenylcarbamoyl)pyrrole-1-heptanoic acid hemicalcium salt.

Hemicalcium salt of [R—(R*,R*)]-2-(4-fluorophenyl)-☐☐-dihydroxy-5-(1-methylethyl)-3-phenyl-4-[(phenylamino)carbonyl]-, 1H-Pyrrole-1-heptanoic acid, a synthetic HMG-CoA reductase inhibitor, is used for the treatment of hyperlipidemia and hypercholesterolemia, both of which are risk factors for arteriosclerosis and coronary heart disease. Open dihydroxy carboxylic acid, lactone and various salt forms of [R—(R*,R*)]-2-(4-fluorophenyl)-☐☐-dihydroxy-5-(1-methylethyl)-3-phenyl-4-[(phenylamino)carbonyl]-, 1H-Pyrrole-1-heptanoic acid have been synthesized.

U.S. Pat. No. 5,273,995, describes that [R—(R*,R*)]-2-(4-fluorophenyl)-☐☐-dihydroxy-5-(1-methylethyl)-3-phenyl-4-[(phenylamino)carbonyl]-, 1H-Pyrrole-1-heptanoic acid has surprising inhibition of the biosynthesis of cholesterol. Calcium salt of [R—(R*,R*)]-2-(4-fluorophenyl)-☐☐-dihydroxy-5-(1-methylethyl)-3-phenyl-4-[(phenylamino)carbonyl]-, 1H-Pyrrole-1-heptanoic acid (2:1) which is more suited to formulations and has been recommended as a drug.

U.S. Pat. Nos. 5,003,080; 5,097,045; 5,103,024; 5,124,482; 5,149,837; 5,155,251; 5,216,174; 5,245,047; 5,248,793; 5,273,995; 5,280,126; 5,298,627; 5,342,952; 5,385,929; 5,397,792; European Patent 409,281; and WO 89/07598 describe various processes and key intermediates for preparing atorvastatin.

WO 97/03958 and WO 97/03959 disclose novel crystalline forms of atorvastatin calcium designated as Form I, Form II, Form III and Form IV and method for their preparation which provide more favorable filtration and drying characteristics.

WO 97/03960 and U.S. Pat. No. 6,087,511 describe the procedures for converting the crystalline form of atorvastatin calcium to the amorphous form. The process disclosed therein involve dissolving form I atorvastatin calcium in a non-hydroxylic solvent like tetrahydrofuran or a mixture of tetrahydrofuran and toluene.

WO 00/71116 describes the procedure for converting the crystalline form-I by dissolving it in a non-hydroxylic solvent like tetrahydrofuran and precipitating amorphous atorvastatin calcium by the addition of nonpolar hydrocarbon solvents like, n-hexane, cyclohexane or n-heptane. The process described in the above mentioned patent involves dissolving the crystalline atorvastatin (form-I) in a non hydroxylic solvent like tetrahydrofuran or mixtures of tetrahydrofuran and toluene, followed by removal of the solvents under high temperature (about 90° C.) and high vacuum (about 5 mm). This process may not suitable on a large scale as the conditions used for drying may lead to degradation of the product.

Many of the process disclosed in the above patents does not produce atorvastatin calcium in its amorphous form consistently. Often a mixture of crystalline and amorphous form is obtained which is not suitable for filtration and drying and therefore not a desirable process for large-scale production.

It is the object of the present invention to provide a novel process for the preparation of amorphous atorvastatin calcium, which is unique with respect to its simplicity, cost effectiveness and scalability.

SUMMARY OF THE INVENTION

The instant invention relates to a novel process of the preparation of amorphous atorvastatin calcium.

The novel process of instant invention comprises conversion of compound of Formula II

FORMULA II

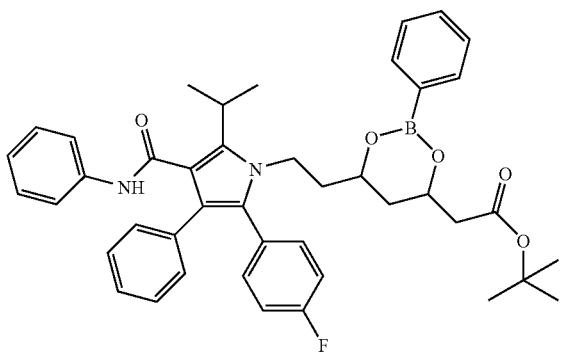

to atorvastatin calcium (Formula I).

FORMULA I

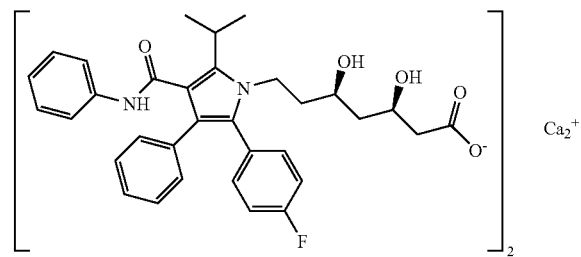

DETAILED DESCRIPTION OF THE INVENTION

The instant process for the preparation of amorphous form of compound of Formula I from a compound of Formula II comprising:

FORMULA I

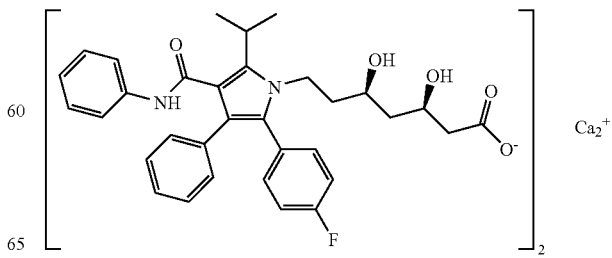

FORMULA II

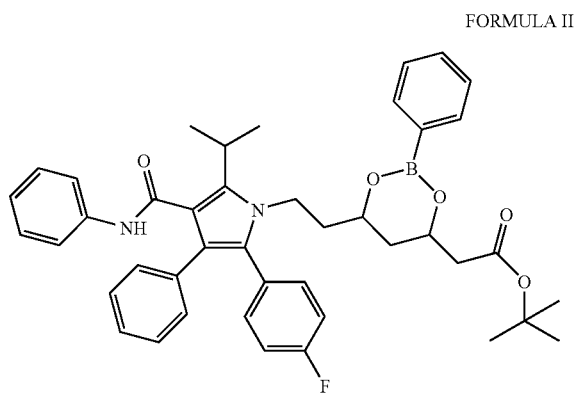

(a) adding aqueous NaOH to the compound of Formula II to get a sodium salt,
(b) dissolving the wet sodium salt in ethyl acetate,
(c) addition of calcium acetate followed by stirring,
(d) collecting the organic layer and concentrating to get a residue,
(e) drying the residue to get amorphous compound of Formula I.

The process where calcium acetate in step (c) is calcium acetate is optionally substituted with calcium chloride.

The process where the amorphous compound of Formula I is vacuum dried.

The novel process of instant invention has following advantages:
1. De-protection of boronate ester and cleavage of tert-butyl ester and formation of calcium salt is done easily in one pot.
2. Simple procedure involving inexpensive Calcium Acetate.
3. An inexpensive method.
4. The process is industrially scaleable.
5. Amorphous atorvastatin calcium is obtained directly without isolation of crude material.

The present invention will now be illustrated by the following examples, which are not intended to limit the effective scope of the claims. Consequently, any variations of the invention described above are not to be regarded as departure from the spirit and scope of the invention as claimed. The present invention has been described in terms of its specific embodiments and various modifications and equivalents will be apparent to those skilled in the art and are intended to be included within the scope of present invention.

EXAMPLES

Example I (6-{2-[2-(4-Fluoro-phenyl)-5-isopropyl-3-phenyl-4-phenylcarbamoyl-pyrrolidin-1-yl]-ethyl}-2-phenyl-[1,3,2]dioxaborinan-4-yl)-acetic acid tert-butyl ester (compound of Formula II, 500 g, 0.7 mol) was dissolved in THF (4 L) and degassed with nitrogen gas for 30 minutes. A solution of sodium hydroxide (142 g) in water (3.57 L) was added to the above solution and refluxed for 2 hours. The reaction mixture was concentrated under vacuum to remove solvent and water (7.5 L) was added followed by MTBE (2.5 L). After separating layers, aqueous was kept under vacuum for 1 hour and the solution was allowed to stand for 12 hrs at room temperature. The precipitate formed (sodium salt of atorvastatin) was filtered and dissolved in ethyl acetate (3.5 L). To the clear organic layer, a solution of calcium acetate (99.4 g) in water (2 L) was added and stirred at 40-45° C. The layers were separated and organic layer was washed with water (5×5 L). The organic layer was evaporated and residue was dried under vacuum to get Atorvastatin Calcium amorphous.

Yield: 380 g.

Example II (6-{2-[2-(4-Fluoro-phenyl)-5-isopropyl-3-phenyl-4-phenylcarbamoyl-pyrrolidin-1-yl]-ethyl}-2-phenyl-[1,3,2]dioxaborinan-4-yl)-acetic acid tert-butyl ester (compound of Formula II, 10 kg, 14.82 mol), compound of Formula II, was dissolved in THF (80 L) and degassed with nitrogen gas for 30 minutes. A solution of sodium hydroxide (2.84 kg) in water (72 L) was added to the above solution and refluxed for 4 hours. The reaction mixture was concentrated under vacuum to remove solvent and water (150 L) was added followed by MTBE (50 L). After separating layers, aqueous was kept under vacuum for 3 hours and the solution was allowed to stand for 12 hrs at 25-28° C. The precipitate formed (sodium salt of atorvastatin) was filtered and dissolved in ethyl acetate (70 L) To the clear organic layer, a solution of calcium acetate (2 kg) in water (40 L) was added and stirred at 40-45° C. The layers were separated and organic layer was washed with water (5×100 L). The organic layer was evaporated and residue was dried under vacuum to get Atorvastatin Calcium amorphous.

Yield: 7.2 kg

Example III (6-{2-[2-(4-Fluoro-phenyl)-5-isopropyl-3-phenyl-4-phenylcarbamoyl-pyrrolidin-1-yl]-ethyl}-2-phenyl-[1,3,2]dioxaborinan-4-yl)-acetic acid tert-butyl ester (compound of Formula II, 500 g, 0.7 mol) was dissolved in THF (4 L) and degassed with nitrogen gas for 30 minutes. A solution of sodium hydroxide (142 g) in water (3.57 L) was added to the above solution and refluxed for 2 hours. The reaction mixture was concentrated under vacuum to remove solvent and water (7.5 L) was added followed by MTBE (2.5 L). After separating layers, aqueous was kept under vacuum for 1 hour and the solution was allowed to stand for 12 hrs at room temperature. The precipitate formed (sodium salt of atorvastatin) was filtered and dissolved in ethyl acetate (3.5 L). To the clear organic layer, a solution of calcium chloride (60 g) in water (2 L) was added and stirred at 40-45° C. The layers were separated and organic layer was washed with water (5×5 L). The organic layer was evaporated and residue was dried under vacuum to get Atorvastatin Calcium amorphous.

Yield: 350 g.

We claim:
1. A process for the preparation of amorphous form of compound of Formula I from a compound of Formula II comprising:

FORMULA I

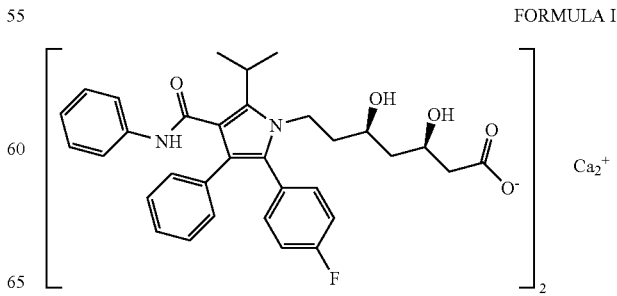

FORMULA II

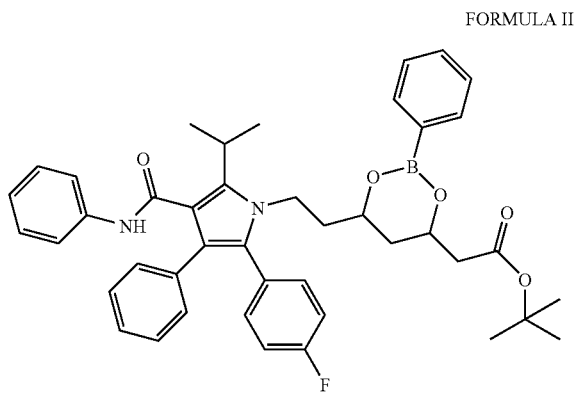

(a) adding aqueous NaOH to the compound of Formula II to get a sodium salt,
(b) dissolving the wet sodium salt in ethyl acetate,
(c) addition of calcium acetate followed by stirring,
(d) collecting the organic layer and concentrating to get a residue,
(e) drying the residue to get amorphous compound of Formula I.

2. A process as in claim 1, wherein calcium acetate in step (c) is calcium acetate is optionally substituted with calcium chloride.

3. A process as in claim 1, wherein the amorphous compound of Formula I is vacuum dried.

4. A process as in claim 1, wherein sodium salt in step (b) is optionally dried and further processed.

* * * * *